United States Patent [19]

O'Lenick, Jr.

[11] Patent Number: 5,717,119
[45] Date of Patent: Feb. 10, 1998

[54] POLYOXYALKYLENE GLYCOL GUERBET ESTERS

[75] Inventor: Anthony J. O'Lenick, Jr., Lilburn, Ga.

[73] Assignee: Lambent Technologies Inc., Norcross, Ga.

[21] Appl. No.: 779,972

[22] Filed: Dec. 23, 1996

Related U.S. Application Data

[63] Continuation-in-part of Ser. No. 548,737, Oct. 26, 1995, Pat. No. 5,639,791, which is a continuation-in-part of Ser. No. 332,135, Oct. 31, 1994, Pat. No. 5,488,121.

[51] Int. Cl.$^6$ .................................................. C07C 53/00
[52] U.S. Cl. ........................ 554/227; 568/606; 568/613
[58] Field of Search ................................ 554/167, 227; 568/606, 613

[56] References Cited

U.S. PATENT DOCUMENTS

| 4,425,458 | 1/1984 | Lindner et al. | 524/314 |
| 4,868,236 | 9/1989 | O'Lenick | 524/308 |

OTHER PUBLICATIONS

Morrision & Boyd, Organic Chemistry, 4th ed., p. 828, 1983.

Primary Examiner—Gary Geist
Assistant Examiner—Deborah D. Carr

[57] ABSTRACT

The present invention deals with the composition of matter and the utilization of certain novel polyoxyalkylene glycol esters which are prepared by the reaction of a guerbet acid and a polyoxylalkylene glycol as emulsifiers.

9 Claims, No Drawings

POLYOXYALKYLENE GLYCOL GUERBET ESTERS

RELATED APPLICATIONS

This application is a continuation in part of Ser. No. 548,737, filed Oct. 26, 1995, now U.S. Pat. No. 5,639,791, which is in turn a continuation in part of Ser. No. 332,135 filed Oct. 31, 1994, now U.S. Pat. No. 5,488,121.

BACKGROUND OF THE INVENTION

1. Field of the Invention

The present invention deals with novel emulsifiers. The compounds are polyoxyalkylene glycol esters of guerbet acids. The introduction of the regiospecific branched guerbet acid portion of the molecule into the compounds of the present invention results in improved emulsification efficiency and improved liquidity of the esters.

2. Description of the Art Practices

Guerbet alcohols have been known for many years. Over the years there have been a number of derivatives patented.

U.S. Pat. No. 4,868,236 to O'Lenick discloses a guerbet citric ester and polymers thereof useful in plastic lubrication.

U.S. Pat. No. 4,425,458 to Lindner and O'Lenick teaches that specific guerbet esters can be used as polycarbonate lubricants.

These materials can be oxidized into acids, which are raw materials for the preparation of the specific polyoxyalkylene glycol esters of the present invention. They possess the critical regiospecific guerbet linkage which when placed into polyoxyalkylene glycol esters results in unexpected improvements in both liquidity and emulsification properties of the resultant esters.

THE INVENTION

This invention relates to the use of a particular group of regiospecific beta branched guerbet acids to prepare a polyoxyalkylene glycol esters made by the reaction of a guerbet acid and a polyoxyalkylene glycol to make a new series of unexpectedly efficient branched esters.

Esters are a class of compounds which find applications in many diverse segments of the chemical industry. One of the problems which is encountered using non-branched fatty acids to make polyoxyalkylene glycol esters is the fact that these materials are waxy solids with relatively high melting points. They possess some desirable surfactant properties, like emulsification, but need to be used in relatively high concentrations. It is very desirable to limit the concentration of surfactant in making emulsions. The emulsifiers used in a water in oil emulsion for example allows for the preparation of emulsion, but the delivery of the oil from the emulsion can be limited by a high level of emulsifier.

The specific structure of the ester determines the functional attributes of the product, including emulsification and liquidity. There are many possible structural variations which can impact upon the performance of esters. We have learned that the presence of a specific beta branching in the acid side of the molecule results in improved properties.

The compounds of the current invention are specific branched esters conforming to the following structure;

R—C(O)—O—(CH$_2$CH$_2$—O)$_x$—(CH$_2$CH(CH$_3$)—O)$_y$—(CH$_2$CH$_2$—O)$_z$—C(O)—R wherein:
R is:

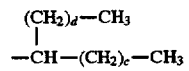

c and d are independently integers ranging from 3 to 14;
x, y and z are independently integers ranging from 0 to 115, with the proviso that x+y+z be greater than 1.

PREFERRED EMBODIMENT

In a preferred embodiment c and d are each 3.
In another preferred embodiment c and d are each 4.
In another preferred embodiment c and d are each 5.
In another preferred embodiment c and d are each 6.
In another preferred embodiment c and d are each 7.
In another preferred embodiment c and d are each 8.
In still another preferred embodiment c and d are each 14.

EXAMPLES

Raw Materials

Guerbet Acids

Guerbet alcohols are oxidized into acids having the same regiospecific beta branched properties. This branching property present in the acid make products useful in the present invention.

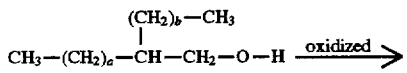

Guerbet Alcohol

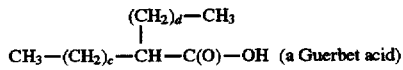

CH$_3$—(CH$_2$)$_c$—CH—C(O)—OH (a Guerbet acid)

Vista Chemical practices the oxidation of guerbet alcohols commercially. The values of c and d were actually determined by analysis and are not dependant upon trade name for meaning.

| Example | Commercial Name | c | d |
|---------|----------------|----|----|
| 1 | Isocarb 10 | 3 | 3 |
| 2 | Isocarb 12 | 4 | 4 |
| 3 | Isocarb 14 | 5 | 5 |
| 4 | Isocarb 16 | 6 | 6 |
| 5 | Isocarb 18 | 7 | 7 |
| 6 | Isocarb 20 | 8 | 8 |
| 7 | Isocarb 32 | 14 | 14 |

Isocarb is a trademark of Vista.

Ester Synthesis

The esterification reaction is carried out using an excess of polyoxyalkylene glycol or acid or more typically using an equivalent of each. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

The ester is prepared by the esterification reaction as shown below:

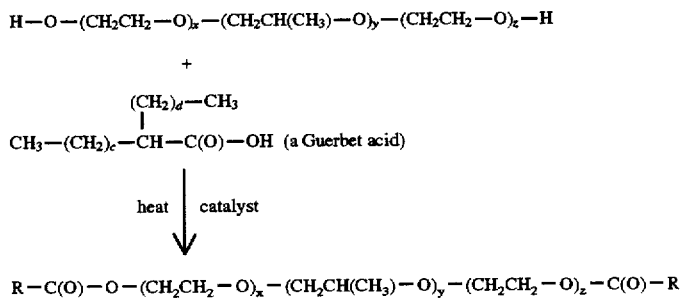

R is:

| Example | x | y | z |
|---|---|---|---|
| 8 | 14 | 0 | 0 |
| 9 | 23 | 0 | 0 |
| 10 | 9 | 0 | 0 |
| 11 | 4 | 0 | 0 |
| 12 | 1 | 0 | 0 |
| 13 | 115 | 0 | 0 |
| 14 | 0 | 1 | 0 |
| 15 | 0 | 17 | 0 |
| 16 | 0 | 115 | 0 |
| 17 | 0 | 1 | 0 |
| 18 | 10 | 10 | 115 |
| 19 | 1 | 1 | 1 |
| 20 | 50 | 10 | 10 |

General Procedure

To the specified number of grams of guerbet acid (examples 1-7) is added the specified number of grams of the specified polyoxyalkylene glycol (Examples 8-20). Next add 0.1% stannous oxylate based upon the total weight of the batch after all ingredients have been charged, under agitation. THe temperature of the mass is raised to 180-200 C. and water is stripped off as formed. The acid value and hydroxyl value drop to vanishingly small values, and the saponification value increases to theoretical.

The products are clear liquids and are liquid to extraordinary temperatures. They exhibit outstanding lubrication properties and are outstanding viscosity index modifiers.

Example 21

To 171.0 grams of guerbet acid (examples 1) is added the 308.0 grams of the specified polyoxyalkylene glycol (Examples 8). Next add 0.1% stannous oxylate based upon the total weight of the batch after all ingredients have been charged, under agitation. The temperature of the mass is raised to 180-200 C. and water is stripped off as formed. The acid value and hydroxyl value drop to vanishingly small values, and the saponification value increases to theoretical.

|  | Polyoxyalkylene Glycol |  | Guerbet Acid |  |
|---|---|---|---|---|
| Example | Example | Grams | Example | Grams |
| 21 | 8 | 308.0 | 1 | 171.0 |
| 22 | 9 | 506.0 | 2 | 199.0 |
| 23 | 10 | 198.0 | 3 | 227.0 |
| 24 | 11 | 88.0 | 4 | 255.0 |
| 25 | 12 | 22.0 | 5 | 283.0 |
| 26 | 13 | 2500.0 | 6 | 311.0 |
| 27 | 14 | 30.0 | 7 | 479.0 |
| 28 | 15 | 501.0 | 7 | 479.0 |
| 28 | 16 | 3393.0 | 6 | 311.0 |
| 30 | 17 | 51.2 | 5 | 283.0 |
| 31 | 18 | 3106.0 | 4 | 255.0 |
| 32 | 19 | 73.5 | 3 | 227.0 |
| 33 | 20 | 2795.0 | 2 | 199.0 |
| 34 | 20 | 2795.0 | 1 | 171.0 |

The compounds of the present invention are liquid esters with outstanding emulsification properties.

I claim:

1. A compound which conforms to the following structure:

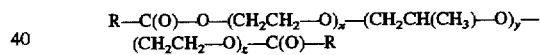

wherein:

R is:

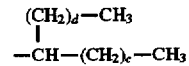

x, y and z are independently integers ranging from 0 to 115, with the proviso that x+y+z be greater than 1;

c and d are each independently integers ranging from 3 to 14.

2. A compound of claim 1 wherein c and d are each 3.
3. A compound of claim 1 wherein c and d are each 4.
4. A compound of claim 1 wherein c and d are each 5.
5. A compound of claim 1 wherein c and d are each 6.
6. A compound of claim 1 wherein c and d are each 7.
7. A compound of claim 1 wherein c and d are each 8.
8. A compound of claim 1 wherein c and d are each 14.
9. A compound of claim 1 wherein x is 22.

* * * * *